United States Patent
Pantazis et al.

(10) Patent No.: US 9,971,136 B2
(45) Date of Patent: May 15, 2018

(54) METHOD AND DEVICE TO ACHIEVE SPATIALLY CONFINED PHOTOINTERACTION AT THE FOCAL VOLUME OF A MICROSCOPE

(71) Applicants: ETH ZÜRICH, Zürich (CH); CALIFORNIA INSTITUTE OF TECHNOLOGY, Pasadena, CA (US)

(72) Inventors: Periklis Pantazis, Oberwil (CH); William P. Dempsey, Sunland, CA (US); Thai V. Truong, Pasadena, CA (US); Scott E. Fraser, Glendale, CA (US); Lada Georgieva, Basel (CH)

(73) Assignees: ETH ZÜRICH, Zürich (CH); CALIFORNIA INSTITUTE OF TECHNOLOGY, Pasadena, CA (US)

(*) Notice: Subject to any disclaimer, the term of this patent is extended or adjusted under 35 U.S.C. 154(b) by 217 days.

(21) Appl. No.: 14/778,618

(22) PCT Filed: Mar. 20, 2014

(86) PCT No.: PCT/EP2014/055669
§ 371 (c)(1),
(2) Date: Sep. 21, 2015

(87) PCT Pub. No.: WO2014/147211
PCT Pub. Date: Sep. 25, 2014

(65) Prior Publication Data
US 2016/0054553 A1  Feb. 25, 2016

Related U.S. Application Data

(60) Provisional application No. 61/804,064, filed on Mar. 21, 2013.

(51) Int. Cl.
*G02B 21/00* (2006.01)
*G02B 5/20* (2006.01)
(Continued)

(52) U.S. Cl.
CPC ..... *G02B 21/0076* (2013.01); *G01N 21/6428* (2013.01); *G01N 21/6458* (2013.01);
(Continued)

(58) Field of Classification Search
CPC .......................... G02B 21/0076; G02B 5/201; G02B 21/0032; G02B 27/141; G01N 21/6428; G01N 21/6458
See application file for complete search history.

(56) References Cited

U.S. PATENT DOCUMENTS 5,674,698 A * 10/1997 Zarling ............... G01N 33/588
422/504
2010/0193673 A1  8/2010 Power et al.
(Continued)

FOREIGN PATENT DOCUMENTS

JP       H10 142151       5/1998

OTHER PUBLICATIONS

Shimomura, O., Johnson, F. H., & Saiga, Y. (1962), Extraction, purification and properties of aequorin, a bioluminescent protein from the luminous hydromedusan, Aequorea. Journal of cellular and comparative physiology, 59(3), 223-239.
(Continued)

*Primary Examiner* — Christine Sung
(74) *Attorney, Agent, or Firm* — Soroker Agmon Nordman

(57) ABSTRACT

The invention relates to a method and a system to achieve spatially (e.g. three-dimensionally) confined photomodulation at the focal volume (50) in a ample (55) mounted in a microscope system, comprising two or more laser light sources (41, 42) emitting light (32, 34) of different wavelengths adapted to excite a material in an identical number of independent excitation steps to a higher vibrational state from which the material relaxes, either emitting a conversion
(Continued)

light to be detected ("photoexcitation") or modulating the spectral properties of the material ("photomodulation").

15 Claims, 14 Drawing Sheets

(51) Int. Cl.
  G02B 27/14 (2006.01)
  G01N 21/64 (2006.01)
  G01N 21/17 (2006.01)
(52) U.S. Cl.
  CPC ......... *G02B 5/201* (2013.01); *G02B 21/0032* (2013.01); *G02B 27/141* (2013.01); *G01N 21/6408* (2013.01); *G01N 2021/1785* (2013.01)

(56) References Cited

U.S. PATENT DOCUMENTS

| | | |
|---|---|---|
| 2011/0036996 A1 | 2/2011 | Wolleschensky et al. |
| 2011/0102787 A1 | 5/2011 | Hess et al. |

OTHER PUBLICATIONS

Heim, R., Prasher, D. C., & Tsien, R. Y. (1994), Wavelength mutations and posttransiational autoxidation of green fluorescent protein. Proceedings of the National Academy of Sciences, 91(26), 12501-12504.
Kilgard, M. P., & Merzenich, M. M. (1995). Anticipated stimuli across skin. Nature.
Tsien, R. Y. (1998), The green fluorescent protein. Annual review of biochemistry, 67(1), 509-544.
Kicheva, A., Pantazis, P., Bollenbach, T., Kalaidzidis, Y., Bittig, T., Jülicher, F., & Gonzalez-Gaitan, M. (2007). Kinetics of morphogen gradient formation, Science, 315(5811), 521-525.
Patterson, G. H., & Lippincott-Schwartz, J. (2002). A photoactivatable GFP for selective photolabeling of proteins and cells. Science, 297(5588), 1873-1877.
Patterson, G. H., & Lippincott-Schwartz, J. (2004). Selective photolabeling of proteins using photoactivatable GFP. Methods, 32(4), 445-450.
Subach, F. V., Patterson, G. H., Manley, S., Gillette, J. M., Lippincott-Schwartz, J., & Verithusha, V. V. (2009), Photoactivatable mCherry for high-resolution two-color fluorescence microscopy. Nature methods, 6(2), 153-159.
Ando, R., Hama, H., Yamamoto-Hino, M., Mizuno. H., & Miyawaki, A. (2002). An optical marker based on the UV- induced green-to-red photoconversion of a fluorescent protein. Proceedings of the National Academy of Sciences, 99(20), 12651-12656.
Gurskaya, N. G., Verkhusha, V. V., Shcheglov, A. S., Staroverov, D. B., Chepumykh, T. V., Fradkov, A. F., . . . & Lukyanov, K. A. (2006). Engineering of a monomeric green-to-red photoactivatable fluorescent protein induced by blue light. Nature biotechnology, 24(4), 461-465.
McKinney, S. A., Murphy, C. S., Hazelwood, K. L., Davidson, M. W., & Looger, L. L. (2009). A brght and photostable photoconvertible fluorescent protein. Nature methods, 6(2), 131-133.
Habuchi. S., Tsutsui. H., Kochaniak, A. B., Miyawaki, A., & Van Oijen, A. M. (2008). mKikGR, a monomeric photoswitchable fluorescent protein. PLoS One, 3(12), e3944.
Chudakov, D. M., Verkhusha. V. V., Staroverov, D. B., Souslova, E. A., Lokyanov, S., & Lukyanov, K. A. (2004). Photoswitchable cyan fluorescent protein for protein tracking. Nature biotechnology, 22(11), 1435-1439.
Andresen, M., Stiel, A. C., Fölling, J. Wenzel, D., Schönle, A., Egner, A., . . . & Jakobs, S. (2008). Photoswitchable fluorescent proteins enable monochromatic multilabel imaging and dual co fluorescence nanoscopy. Nature biotechnology, 26(9), 1035-1040.
Stiel, A. C., Andresen, M., Bock, H., Hilbert, M., Schilde, J., Schönle, A., . . . & Jakobs, S. (2008). Generation of monomeric reversibly switchable red fluorescent proteins for far-field fluorescence nanoscopy. Biophysical journal, 95(6), 2989-2997.
Adam, V., Lelimousin, M., Boehmer S., Desfonds, G., Nienhaus, K., Field, M. J., . . . & Bourgeois, D. (2008). Structural characterization of IrisFP, an optical highlighter undergoing multiple photo-induced transformations. Proceedings of the National Academy of Sciences, 105(47), 18343-18348.
Pantazis, P., & GonzÃAlez-GaitÃAn, M. (2007). Localized multiphoton photoactivation of paGFP in Drosophila wing imaginal discs. Journal of biomedical optics, 12(4), 044004-044004.
Stark, D. A., & Kulesa, P. M. (2007). An in vivo comparison of photoactivatable fluorescent proteins in an avian embryo model. Developmental Dynamics, 236(8), 1583-1594.
Zernicka-Goetz, M. (2011). Proclaiming fate in the early mouse embryo. Nature cell biology, 13(2), 112-114.
Betzig, E., Patterson, G. H., Sougrat, R., Lindwasser, O. W., Olenych, S., Bonifacino, J. S., . . . & Hess, H. F. (2006). Imaging intracellular fluorescent proteins at nanometer resolution. Science, 313(5793), 1642-1645.
Hofmann, M., Eggeling, C., Jakobs. S., & Hell, S. W. (2005). Breaking the diffraction barrier in fluorescence microscopy at low light intensities by using reversibly photoswitchable proteins. Proceedings of the National Academy of Sciences of the United States of America, 102(49), 17565-17569.
Hell. S. W., & Wichmann, J. (1994). Breaking the diffraction resolution limit by stimulated emission: stimulated-emission-depletion fluorescence microscopy. Optics letters, 19(11), 780-782.
Gustafsson, M. G., Shao, L., Carlton, P. M., Wang, C. R., Golubovskaya, I. N., Cande, W. Z., . . . & Sedat, J. W. (2008), Three-dimensional resolution doubling in wide-field fluorescence microscopy by structured illumination. Biophysical journal, 94(12), 4957-4970.
Hess, S. T., Girirajan, T. P., & Mason, M. D. (2006). Ultra-high resolution imaging by fluorescence photoactivation localization microscopy. Biophysical journal, 91(11), 4258-4272.
Rust, M. J., Bates, M., & Zhuang, X. (2006). Sub-diffraction-limit imaging by stochastic optical reconstruction microscopy (STORM). Nature methods, 3(10), 793-796.
Shtengel, G., Galbraith, J. A., Galbraith, C. G., Lippincott-Schwartz, J., Gillette, J. M., Manley, S., . . . & Hess, H. F. (2009). Interferometric fluorescent super-resolution microscopy resolves 3D cellular ultrastructure. Proceedings of the National Academy of Sciences, 106(9), 3125-3130.
Pavani, S. R. P., Thompson, M. A., Biteen, J. S., Lord, S. J., Liu, N., Twieg, R. J., . . . & Moerner, W. E. (2009). Three-dimensional, single-molecule fluorescence imaging beyond the diffraction limit by using a double-helix point spread function. Proceedings of the National Academy of Sciences, 106(9), 2995-2999.

\* cited by examiner a)

b)

a) b)

METHOD AND DEVICE TO ACHIEVE SPATIALLY CONFINED PHOTOINTERACTION AT THE FOCAL VOLUME OF A MICROSCOPE

This invention was made with government support under grant awarded by the National Institutes of Health. The government has certain rights in the invention.

TECHNICAL FIELD

The present invention relates to a method to achieve spatially confined photointeraction, particularly photomodulation or photoexcitation, at the focal volume of a microscope, especially through dual-laser illumination of samples. The invention also relates to a system for application of a reliable method of photointeraction—particularly conversion, photomodulation or photoexcitation—by illuminating the probe, particularly a fluorescent protein (FP), simultaneously with at least two preferably focused light sources, particularly continuous wave lasers, in a microscope setup, preferably a scanning confocal microscope setup.

PRIOR ART

O. Shimomura, F. H. Johnson, Y. Saiga, J Cell Comp Physiol 59, 223 (1962) reported the green fluorescent protein (GFP) in 1962. Illumination of light with a certain spectral band can cause a "photointeraction" event within the green fluorescent protein, which is defined by photons interacting with the material (GFP in this case), causing a response that can be measured. In the case of GFP, the photointeraction leads to the emission of a green photon that can be detected, in a process termed "fluorescence". However, its usefulness in biological research became apparent only after it was demonstrated that the photo physical properties of the protein could be improved and more colors could be generated by selective mutation as shown by two articles by R. Heim, D. C. Prasher, R. Y. Tsien, PNAS 91, 12501 (1994) and R. Heim, A. B. Cubitt, R. Y. Tsien, Nature 373, 663 (1995). Since this advance, fluorescent proteins (FPs) in a variety of color spectra have been used in many biological contexts, including monitoring protein expression and localization in cells as shown by R. Y. Tsien, Annu Rev Biochem 67, 509 (1998) as well as quantifying protein trafficking in vivo as disclosed in A. Kicheva et al., Science 315, 521 (2007).

In order to broaden the appeal of FPs, three varieties of proteins were developed:
  photoactivatable fluorophores disclosed by G. H. Patterson, J. Lippincott-Schwartz, Science 297, 1873 (2002), G. H. Patterson, J. Lippincott-Schwartz, Methods 32, 445 (2004) and F. V. Subach et al., Nature Methods 6, 153 (2009), which shift from a non-fluorescent state to a fluorescent state after UV irradiation;
  photoconvertible fluorophores disclosed by R. Ando, H. Hama, M. Yamamoto-Hino, H. Mizuno, A. Miyawaki, PNAS 99, 12651 (2002), N. G. Gurskaya et al., Nature Biotechnology 24, 461 (2006), S. A. McKinney, C. S. Murphy, K. L. Hazelwood, M. W. Davidson, L. L. Looger, Nature Methods 6, 131 (2009), S. Habuchi, H. Tsutsui, A. B. Kochaniak, A. Miyawaki, A. M. van Oijen, PLoS ONE 3, 3944 (2008) and D. M. Chudakov et al., Nature Biotechnology 22, 1435 (2004), which shift irreversibly from one visible excitation/emission spectrum to a new excitation/emission spectrum after UV irradiation; and
  photoswitchable proteins disclosed by M. Andresen et al., Nature Biotechnology 26, 1035 (2008), A. C. Stiel et al., Biophysical Journal 95, 2989 (2008), and V. Adam et al. PNAS 105, 18343 (2008); which can shift between different excitation/emission spectra reversibly.

In these cases, the "photointeraction" of absorbed photons of light within the chromophore of the FP or the probe results in the modulation of the spectral properties of the FP or the probe itself. These three subsets of FPs are useful for a variety of applications, including in vivo studies disclosed by P. Pantazis, M. González-Gaitán, Journal of Biomedical Optics 12, 044004 (2007), D. A. Stark, P. M. Kulesa, Developmental Dynamics 236, 1583 (2007) and N. Plachta, T. Bollenbach, S. Pease, S. E. Fraser, P. Pantazis, Nature Cell Biology 13, 117 (2011) and even sub-diffraction limited microscopy (e.g. PALM, RESLOFT, STED, 3D-SIM, FPALM, STORM, iPALM, DH-PALM) in publications by E. Betzig et al., Science 313, 1642 (2006), M. Hofmann, C. Eggeling, S. Jakobs, S. W. Hell, PNAS 102, 17565 (2005), S. W. Hell, J. Wichmann, Optics Letters 19, 780 (1994), M. G. Gustafsson et al., Biophysical Journal 94, 4957 (2008), S. T. Hess, T. P. Girirajan, M. D. Mason, Biophysical Journal 91, 4258 (2006), M. J. Rust, M. Bates, X. Zhuang, Nature Methods 3, 793 (2006), G. Shtengel et al., PNAS 106, 3125 (2009) and S. R. P. Pavani et al., PNAS 106, 2995 (2009).

SUMMARY OF THE INVENTION

Based on the prior art it is an object of the invention to develop and implement a method and a system, particularly a microscope system, to achieve spatially confined photomodulation, or photoexcitation at the focal volume of a microscope, especially through dual-laser illumination of samples.

For simplicity and to illustrate the novel multi-laser spectral shift (i.e. photoactivation, photoconversion, or photoswitching) technique, the present application puts its focus on two varieties of FPs as exemplary samples; however, it is noted that this procedure is applicable to all other varieties of photoactivatable/photoconvertible/photoswitchable proteins listed above as well as any other probe (e.g. organic, inorganic, combination of organic/inorganic, colloidal etc.) not mentioned that falls under these categories. Photoconvertible proteins are convenient varieties to work with for cell culture and in vivo studies, since they already brightly fluoresce in the visible light spectrum before conversion with UV light. Dendra2, expressed as a monomer hereafter referred to simply as Dendra2, and Kaede, expressed as a homotetramer, are two useful coral-derived variants of these photoconvertible FPs, which are shown in N. G. Gurskaya et al., Nature Biotechnology 24, 461 (2006) and R. Ando, H. Hama, M. Yamamoto-Hino, H. Mizuno, A. Miyawaki, PNAS 99, 12651 (2002). The monomeric property of Dendra2 makes it especially useful in protein fusion experiments, because the FP itself will not cause unnatural binding events between fusion partners. These two proteins have been used in a variety of biological applications, including neuroscience as used in A. B. Arrenberg, F. D. Bene, H. Baier, PNAS 106, 17968 (2009), K. C. Flynn, C. W. Pak, A. E. Shaw, F. Bradke, J. R. Bamburg, Developmental Neurobiology 69, 761 (2009), T. Sato, M. Takahoko, H. Okamoto, Genesis 44, 136 (2006) and D. O. Wang et al., Science 324, 1536 (2009), plant cell studies as shown in K. Martin et al., The Plant Journal 59, 150 (2009) and S. C. Brown et al., The Plant Journal 63, 696 (2010), and interrogations of intracellular dynamics as disclosed by D. M. Chudakov, S. Lukyanov, K. A. Lukyanov, Biotechniques 42, 553 (2007) and M. M. Falk, S. M. Baker, A. M. Gumpert, D. Segretain, I. Robert W Buckheit, Molecular Biology of the Cell 20, 3342 (2009).

TABLE 1

| Protein | Excitation Peak (Before Conversion) | Emission Peak (Before Conversion) | Excitation Peak (After Conversion) | Excitation Peak (After Conversion) |
|---|---|---|---|---|
| Dendra2 | 490 | 507 | 553 | 573 |
| Kaede | 508 | 518 | 572 | 580 |

The excitation emission peaks for the Dendra2 and Kaede proteins are listed in table 1 above.

The conversion observed with these proteins is made possible by a physical bond cleavage of amino acid residues that make up the chromophore within the core of the FP itself. In the case of Kaede, UV exposure induces a β-elimination reaction of the His62 residue of the His62-Tyr63-Gly64 chromophore, resulting in the fluorescence spectrum shift, shown in H. Mizuno et al., Molecular Cell 12, 1051 (2003). A similar β-elimination reaction occurs within the His62-Tyr63-Gly64 chromophore of Dendra2; differences in the amino acid residues supporting the Dendra2 chromophore cause the fluorescence spectral shift particular to this protein as disclosed in V. Adam, K. Nienhaus, D. Bourgeois, G. U. Nienhaus, Biochemistry 48, 4905 (2009). In fact, this β-elimination reaction seems to be a common cause of spectral shifts in photoconvertible proteins, including mKikGR and mEos2 as shown in D. M. Chudakov, S. Lukyanov, K. A. Lukyanov, Nature Protocols 2, 2024 (2007), J. Wiedenmann et al., PNAS 101, 15905 (2004). The cleavage reaction of the chromophores in these photoconvertible proteins contrasts with the behavior of the photoactivatable protein paGFP, which undergoes a neutral-to-anionic Ser65-Tyr66-Gly67 chromophore transition after UV exposure as shown in G. H. Patterson, J. Lippincott-Schwartz, Science 297, 1873 (2002), maintaining the bonds between each amino acid within the chromophore. It is noted that a similar decarboxylation reaction seems to be present in the spectral shift of the photoconvertible protein PS-CFP after UV exposure as shown in D. M. Chudakov et al., Nature Biotechnology 22, 1435 (2004). Another type of spectral shift can also occur when considering photoswitchable proteins such as Dronpa and Padron, which undergo a cis-trans isomerization of the chromophore as a result of UV illumination, shown in M. Andresen et al., Nature Biotechnology 26, 1035 (2008) and A. C. Stiel et al., Biophysical Journal 95, 2989 (2008).

Though it has been shown that KikGR can be photoconverted with femtosecond pulsed two-photon microscopy as shown in H. Tsutsui, S. Karasawa, H. Shimizu, N. Nukina, A. Miyawaki, EMBO Rep 6, 233 (2005), the amount of scan time necessary to achieve efficient conversion is 1000-fold the time necessary to convert with 405 nm light alone as particularly mentioned in K. Hatta, H. Tsujii, T. Omura, Nature Protocols 1, 1 (2006). Additionally, two-photon conversion was not demonstrated with the monomeric variety of KikGR, which is called mKikGR in S. Habuchi, H. Tsutsui, A. B. Kochaniak, A. Miyawaki, A. M. van Oijen, PLoS ONE 3, 3944 (2008). The disadvantage of not being able to achieve 3D confined conversion drastically limits the usefulness—for example, (1) photoconversion a) cannot be achieved as deeply as with near infrared two photon conversion, since UV and blue light is highly scattered and absorbed by biological samples and b) with near UV light can be a source of photobleaching and phototoxicity at high laser power and/or at high exposure, and (2) the precision of the photoconversion is limited due to the widespread conversion of protein above and below the focal plane in a confocal imaging modality, etc.—of these and other similar photoconvertible proteins for in vivo applications, which explains why most studies using Dendra2 and Kaede are performed in culture.

We discovered that at least dual-laser illumination using a range of wavelengths results in efficient photomodulation of photoconvertible fluorescent proteins such as Dendra2 and Kaede. In this document, we expand this observation to enable 3D confined photointeractions within a fluorescent material. In the case of photoconversion, we define the photons interacting with the material as being either "priming" or "converting". A "priming" photon refers to the photon required to elevate electrons within the reactive region of the fluorescent molecule or probe to an initial set of energy levels particularly comprised in an excited state of the probe. The "converting" photon particularly brings electrons to a higher set of energy levels, particularly comprised as well in an excited state of the molecule, which then enables the material to undergo efficient photomodulation. This photointeraction with a particular material can be easily extrapolated into a multi-beam modality, where the additional light sources are considered as additional "converting" photons. Importantly, the same setups envisioned in this document may also be used to achieve confined excitation within the sample in the case where the material can be engineered to require multiple sequential absorption events before the emission of a fluorescence photon. In the case of 3D confined excitation, the signal from a fluorescent source or the probe will only be produced at the focus, where the laser light comprising the "priming" and the "converting" photons is superimposed, overlaps or intersects.

According to the invention a method for spatially confined photomodulation or photoexcitation at a focal volume of a microscope system is claimed, comprising the steps:
    providing means to generate a priming laser light beam each comprising a different priming wavelength band and a converting laser light beam comprising a conversion wavelength band different to the priming wavelength band,
    providing a sample, comprising a photoexcitable probe, wherein said probe comprises a low energy level, a primed energy level having a higher energy than the low energy level,
    illuminating the probe with the priming laser light beam, such that the probe is transitioned by photointeraction with the priming laser light beam from the low energy level to a primed energy level in at least one excitation step,
    illuminating the probe with the converting laser light beam such that the probe transitions to a photomodulated state altering the spectral properties of the probe or such that said probe transitions under the particularly spontaneous emission of a photon to the low energy level.

The latter process is dubbed photoexcitation.

Such a microscope system can for example be a microscope.

A means to generate laser light of a priming and a conversion wavelength band can be for example several independent laser light sources or lasers.

A wavelength band comprises a center wavelength and around said center wavelength other wavelengths are emitted within a narrow wavelength band. Such a wavelength band measures usually only a few nanometers in spectral width, depending on the type of laser or laser light source, but could extend considerably if for example a so-called supercontinuum laser source is used. The priming and the conversion wavelength bands are particularly separated from each other so that they do not overlap spectrally. Such lasers or laser light sources are well known in the state of the art. The laser light is particularly emitted in the form of laser light beams, particularly such that the laser light is collimated. Furthermore the priming photons are comprised in the laser light of the priming wavelength band and the converting photons are comprised in the laser light of the conversion wavelength band of the converting laser light beam.

A "level" of the probe in this context might also refer to an energy level, or a set of energy levels, particularly vibrational energy levels. Also, an energy level can be a "state" of the probe, such as for example the ground state, a triplet or a singlet state of the probe.

The photoexcitable probe might comprise only a single molecule, but can contain a plurality of such molecules or a variety of photoexcitable molecules. Said probe is of the kind of FP, organic, inorganic or colloidal as mentioned above. It is noted that the photointeraction, of the laser light and the probe particularly comprises absorption and or conversion resulting in the above described effects.

The process of transitioning to the photomodulated state is particularly referred to as photomodulation. In this context photoexcitation particularly refers to the fact that the probe is only emitting a photon when both the priming and the converting laser light beams photointeract with the probe, particularly within a certain time window—typically not more than 5 ms to 10 ms. Therefore this process is different to the well-known stimulated emission process where emission of a photon is forced by applying a second (depletion) beam to the probe, but the emission of a particularly fluorescence photon usually occurs also when no depletion (converting) beam is applied. Furthermore the mechanism of the present invention does explicitly not invoke a stimulated emission process, as the wavelength band of the converting laser light beam and the wavelength of the emitted photon from the probe are particularly different when applying the method according to the invention (in stimulated emission the wavelength of the depletion beam and the emitted photon are identical) and also the converting laser light beam particularly does not de-excite the probe by stimulated emission according to the invention.

Furthermore it is noted that the transition from the low energy level to the primed energy level and the conversion energy level is achieved particularly by linear absorption, excitation and/or de-excitation processes.

The low energy level, the priming energy levels, the conversion energy level and the photomodulated state particularly comprise vibrational energy bands or sets of energy levels or virtual states such as for example found in second harmonic generation (SHG).

The conversion energy level is particularly an excited state up to which the probe is excited, and is particularly energetically highest from all excited states/priming energy levels, that are excited by the priming or converting laser light beams. It is further noted that said conversion energy level is particularly not accessible by photointeraction with either the "priming" or "converting" photon alone, i.e. the probe can only be excited/photomodulated by the combination of the priming and conversion wavelength bands (and therefore a plurality of different photon energies).

The photomodulated state is particularly characterized in altering the spectral properties of the probe. These spectral properties particularly comprise the excitation/absorption and/or emission spectrum of the probe. It is noted that said alteration of the spectral properties, is particularly due to an alteration of the probes electronic or molecular structure itself (e.g. cis-trans isomerization as mentioned above), though it is noted that particularly photobleaching or photodestruction of the probe (leaving the probe in an irreversible non-fluorescent/luminescent state) is not referred to as altering the spectral properties in this context.

In a preferred embodiment of the invention in case the probe emits a photon upon illumination of the probe with the priming and the converting laser light beam (that is particularly the case for photoexcitation), said photon stems from a spontaneous emission process (as opposed to a stimulated emission process), particularly from fluorescence, phosphorescence or luminescence and wherein particularly the wavelength of the emitted photon is different to the wavelength band of the converting laser light beam and/or the priming laser light beam and that the converting or priming laser light beam is particularly not inducing a stimulated emission process in the probe.

A preferred embodiment of the invention comprises also a plurality of priming or converting laser light beams all comprising a different priming or converting wavelength band.

In a preferred embodiment of the invention the probe further comprises a conversion energy level having a higher energy than the low energy level and the priming energy level, and wherein under the illumination of the probe with the converting laser light beam, said probe transitions from the primed energy level to the conversion energy level from where the probe transitions to said photomodulated state or from where said probe transitions under the emission of a photon from said conversion energy level to the low energy level.

These excitation or photointeraction steps are particularly independent from each other as far as the probe resides in the primed energy level from where it can be transitioned to the conversion energy level or transitioned to the photomodulated state. The time the probe resides in such a primed or a priming energy level depends on the nature of said state or level. It can particularly range from nanoseconds up to micro- or milliseconds.

In another preferred embodiment of the invention the photomodulated state is a photoconverted, photoactivated or photoswitched state of the probe (as they particularly have been described for the various kinds of FPs above).

In a preferred embodiment of the invention the probe comprises a photoconvertible, photoswitchable or photoactivatable protein, particularly Dendra2 or Kaede. Dendra2 is particularly described in (N. G. Gurskaya et al., Nature Biotechnology 24, 461 (2006) and V. Adam et al., Biochemistry 48, 4905 (2009) in detail. Particularly the proteins with the uniprot numbers Q8T6U0 (Dendra) and Q8I6J8 (Kaede) are suitable probes, particularly in their monomeric (Dendra2) respectively homotetrameric form (Kaede).

It is preferred that the probe is illuminated simultaneously or sequentially with the priming laser light beam and the converting laser light beam.

Preferably the laser light beams comprising the priming and conversion wavelength band are superimposed at the focal volume of the microscope system in such a way, that the laser light of each wavelength band is superimposed only at the focal volume.

In a preferred embodiment of the invention the priming laser light beam and the converting laser light beam are focused within or onto the focal volume of the microscope system particularly such that the converting laser light beam and the priming laser light beam are superimposed with each other only within the focal volume.

This geometry of exciting/photomodulating the probe ensures spatially confined photoexcitation or photomodulation at the focal volume, as outside of the focal volume no photoexcitation or photomodulation takes place efficiently, as for the photoexcitation or photomodulation to happen, particularly all (priming and conversion) wavelength bands have to illuminate the probe.

If one of these wavelength bands is missing within the focal volume, the photomodulation or photoexcitation process is unlikely to happen.

In a preferred embodiment of the invention the probe is illuminated with a third laser light beam comprising a third wavelength band and wherein said third laser light beam is either a second priming laser light beam or a second converting laser light beam.

If the third laser light beam is a converting laser light beam, it particularly serves for converting the probe to the photomodulated level or to achieve a photoexcitation process. In case the third laser light beam is a priming laser light beam, it particularly adds an excitation step in order to excite the probe to the primed energy level.

Furthermore the invention comprises a microscope system for carrying out the method according to the invention, wherein the microscope system comprises:
  means for generating a priming laser light beam of a priming wavelength band and a converting laser light beam of a conversion wavelength band different to the priming wavelength band,
  particularly means for guiding the priming and the converting laser light beam along a light path of the microscope system,
  preferably a detection unit for detecting photons emanating from a probe of the microscope system, if a probe is arranged on the microscope system,
wherein the microscope system comprises a photoexcitation device that is designed to superimpose the priming laser light beam and the conversions laser light beam within the focal volume of the microscope system, such that the priming laser light beam and the converting laser light beam intersect, overlap or are superimposed only within the focal volume.

It is important to note, that the term "only within the focal volume" has to be understood, such, that the laser light beams might overlap in regions of the microscope system to which the probe is not exposed, e.g. in the light path of the microscope system were the laser beams are guided towards for example the focusing lens, the probe or the focal volume respectively.

It is noted that superimposing, intersecting or overlapping are used as equivalent terms throughout this document.

The effective focal volume is therefore particularly the volume given by the intersection of the laser light beams.

A laser light beam in this context is laser light particularly in a collimated, near collimated or focused state.

The focal volume particularly includes also geometries that are essentially flat i.e. 2D is a focal volume in this context as well. Furthermore, particularly the image produced from the focal volume is defined by the photons that are detected only from the small volume where the priming and converting photons interact.

In a preferred embodiment of the invention said photoexcitation device comprises a first objective lens and a first optical element arranged before, after or in the first objective lens, particularly in a filter cube of the microscope system or threaded on the first objective lens, wherein said first optical element comprises a first and a second portion, designed to superimpose the priming and the converting laser light beam only within the focal volume if the priming and the converting laser light beam are passed through said first optical element and the first objective lens, wherein the first portion of the optical element particularly is adapted to transmit only the priming laser light beam and the second portion of the optical element is adapted to transmit only the converting laser light beam, wherein said portions particularly comprise dichroic mirrors.

In an especially preferred embodiment of the invention the first and the second portion of the first optical element are arranged concentrically around a common center of the first and the second portion of the first optical element or arranged such that they each form a halve of the first optical element.

In another preferred embodiment of the invention the photoexcitation device comprises a first lens, particularly an objective lens and a first optical element arranged before, after or in the first lens, particularly in a filter cube of the microscope system or threaded on the first lens, and a second lens and a second optical element arranged before, after or in the second lens, particularly in a filter cube of the microscope system or threaded on the second lens, and wherein the first and the second optical element are designed such that if the priming laser light beam is passed through the first optical element and the first lens and the converting laser light beam is passed through the second optical element and the second lens, the priming and the converting laser light beam are superimposed only within the focal volume.

In another preferred embodiment according to the invention said photoexcitation device comprises a first and a second lens, particularly objective lens, wherein the first and the second lens are arranged such, that the priming and the converting laser light beam are superimposed only within the focal volume if the priming laser light beam is passed through the first lens and the converting laser light beam is passed through the second lens, wherein the first and the second lens are arranged such that the priming and the converting laser light beam are propagated at an angle to each other, particularly at an angle of 90 degree.

It can be advantageous that either the priming or the converting laser light beam is shaped as a light sheet after passing through the first or second lens, and wherein particularly the respective other laser light beam (i.e. the converting or priming laser light beam) is focused onto the light sheet orthogonally.

The light sheet might be generated by a scanner comprised by the microscope system designed for moving the priming or the converting laser light beam to generate said light sheet. Alternatively the light sheet might be generated by use of a cylindrical lens, i.e. the first or second lens might be cylindrical.

The respective other laser light beam (converting or priming) is focused particularly orthogonally on the light sheet, so that the priming and the converting laser light beams are superimposed only at the focal volume, that is particularly defined by the intersection of the converting and priming laser light beam. The orthogonally focused laser light beam might be focused onto a small number of well separated points onto the light sheet to generate the event in a plurality of focal volums.

In another preferred embodiment, the priming or the converting laser is shaped such, that after passing through the first respectively the second lens, the probe is illuminated in so-called wide-field illumination mode, i.e. the respective laser light beam is close to or collimated after passing through the first or second lens. The other laser light beam (either the converting or the priming laser light beam) that is not collimated, is focused onto the focal volume. A third laser light beam, converting or priming, is preferably focused onto the focal volume such that a spatially confined conversion or photoexcitation is taking place only at the focal volume where the converting, priming and particularly the third laser light beam overlap.

In a preferred embodiment of the invention the priming laser beam comprises a priming wavelength band that must be determined empirically for a given probe (e.g. found to be in the blue or blue/green visible spectrum for Dendra2), and the converting laser beam comprises a conversion wavelength band that must be determined empirically for a given probe (e.g., found to be in the visible far red or near infrared regime for Dendra2).

In a preferred embodiment of the invention, a piece of optical equipment, that is the photoexcitation device, that enables 3D confined conversion, i.e. photomodulation as well as confined optical excitation (for e.g., fluorescence, luminescence) in a select focal volume is provided, wherein two light sources (e.g., lasers) of differing wavelength meet. The device consists of an e.g., metal or plastic base that fits within the light path of a microscope system such that the laser light comprising the "priming" and "converting" photons is superimposed at the focus. Particularly said device fits a microscope objective in one end and the objective port of a microscope system on the other end. The device might comprise two optical filter elements, particularly dichroic mirrors, one that passes the "converting beam", i.e. the converting laser light beam, and another that passes the "priming beam", i.e. the priming laser light beam. such that the incoming lasers are sub-apertured into the objective lens, and the lasers only meet at the focus within the sample. In one preferred embodiment two dichroic mirrors are in the device, one that passes the "converting beam" and another that passes the "priming beam" such that the incoming lasers are sub-apertured into the objective lens, and the lasers only meet at the focus within the sample. One simple implementation of this photoexcitation device is the splitting of two circular mirrors into half circles that fit into the metal or plastic base.

An alternate implementation can also be envisioned with concentric glass rings, or dichroic mirrors, within the device. The outer diameter of a larger donut mirror 'X' and the size of the smaller disk mirror 'Y' can have a wide range of variation, because the primed conversion or excitation event at the focus, that is the focal volume, can be tuned to the specific size of the mirrors in the device by manipulating the laser attenuation so that more or less power reaches the sample. In practice, the total surface area of the outer and inner dichroics may be approximately the same, but the ratio of individual areas to the total area of the combined mirrors can vary as much as, 100:1, 10:1 or 5:1 in either direction (i.e., in the latter case the outer mirror can have at minimum 20% of the total area, leaving the inner mirror with 80% of the total area, or vice versa).

Note that in either embodiment, the device is intended for combining two lasers at or within the focus, but a device of similar design (e.g., multiple concentric donut-shaped dichroic mirrors and a final disk in the center, a device with glass dichroic mirrors divided into multiple regions using some other geometry, etc.) is provided for applications requiring more than two lasers to achieve primed conversion or confined excitation. It is possible to arrange such mirrors in a filter cube of the microscope system.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
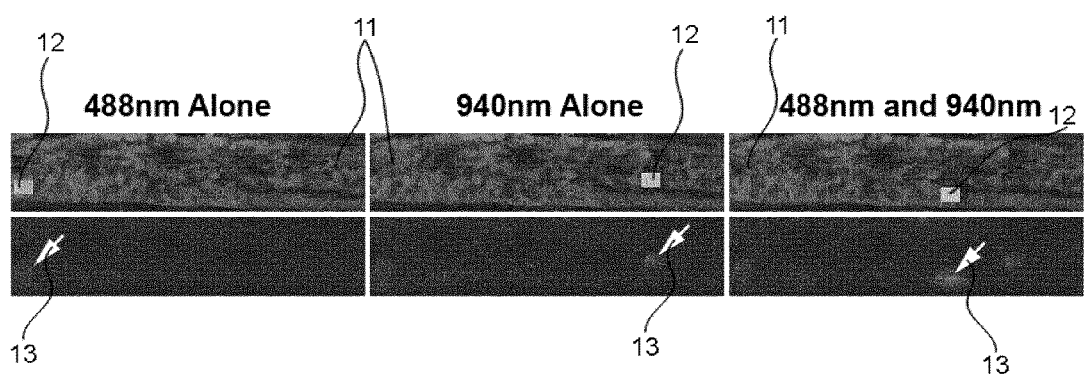
FIG. 1 shows a primed conversion/photomodulation of Kaede.

FIG. 1 shows the primed conversion of Kaede. In FIG. 1, a ~2dpf zebrafish labeled with cytoplasmic Kaede was photoconverted in the developing neural tube region of the trunk in comparably bright spots. The top row of images shows three images: cytoplasmic unconverted Kaede filling the images as reference numerals 11 along with square areas 12 where the photoconversion was attempted. The bottom row of images shows the status after attempted photoconversion, checking whether Kaede was photoconverted. Arrows 13 indicate where the photoconversion should have been, if it was successful. Left Column: Attempting to photoconvert a region 12 using 488 nm alone. As can be seen in the bottom left panel, no significant photoconversion can be observed. The Middle Column shows the attempt to photoconvert a region 12 using 940 nm alone. As can be seen in the bottom center panel, no significant photoconversion can be observed. The Right Column finally shows the attempt to photoconvert a region 12 by illuminating the region simultaneously with 488 nm (priming beam) and 940 nm (converting beam) using the same power of each individual laser as in the left and middle columns. As can be seen, the photoconverted region in the bottom right panel is brighter than when photoconverted with one laser alone. Note that the 940 nm illumination was achieved here using a two-photon laser system, but the same primed conversion event would still occur with a continuous-wave laser illumination at the same wavelength.

Whereas paGFP as well as certain other FPs can be activated using femtosecond pulsed two-photon microscopy to achieve 3D confinement in biological samples as in P. Pantazis, M. Gonzalez-Gaitán, Journal of Biomedical Optics 12, 044004 (2007) or K. Hatta, H. Tsujii, T. Omura, Nature Protocols 1, 1 (2006), certain proteins capable of a spectral shift such as Dendra2 and Kaede cannot be photoconverted with conventional two-photon microscopy, possibly due to the differences in chromophore reorganization as a result of light-induced activation/conversion mentioned previously in FIG. 1.

Only one group reported apparently a successful two-photon photoconversion with Kaede in H. Tsutsui, S. Karasawa, H. Shimizu, N. Nukina, A. Miyawaki, EMBO Rep 6, 233 (2005); however, another study could not reproduce, or only very inefficient this result as published in S. C. Brown et al., The Plant Journal 63, 696 (2010), therefore the previously prior art seems not to be a valid prior art.

Figure 2:
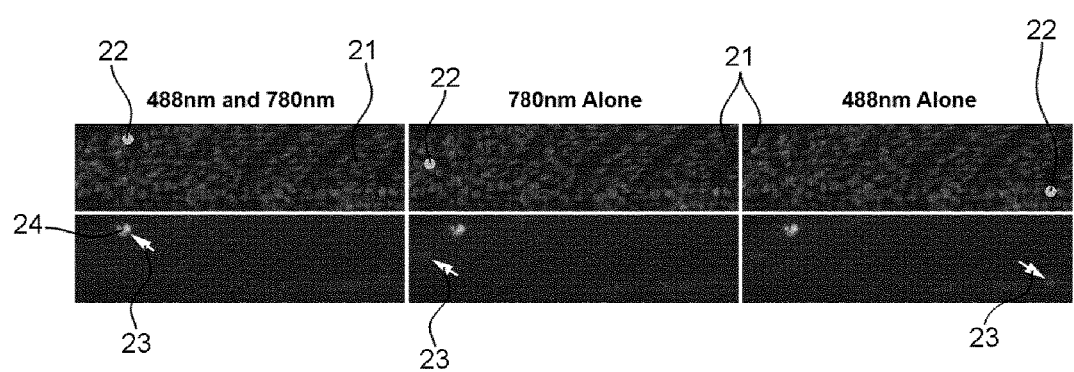
FIG. 2 shows a primed conversion/photomodulation of Dendra2.

FIG. 2 shows Primed Conversion of Dendra2. In this FIG. 2, a ~2dpf zebrafish labeled with H2B-Dendra2 (to see the nuclei) was photoconverted in the somite region of the trunk in comparably bright nuclei. Top row of images: cytoplasmic unconverted Dendra2 21 along with circular areas 22 where the photoconversion was attempted. Bottom row of images: After attempted photoconversion, checking whether Dendra2 was photoconverted. Arrows 23 indicate where the photoconversion should have been, if it was successful. Left Column: Attempting to photoconvert a region 22 by illuminating the region simultaneously with 488 nm (priming beam) and 780 nm (converting beam) using the same power of each individual laser as in the left and middle columns. As can be seen in FIG. 2, the photoconverted region 24 in the bottom left panel is much brighter than when photoconverted with one laser alone (bottom middle and bottom right panels). Middle Column shows the attempt to photoconvert a region 22 using 780 nm alone. As can be seen in the bottom center panel, no significant photoconversion can be observed. Right Column shows the attempt to photoconvert a region 22 using 488 nm alone. As can be seen in the bottom right panel, no significant photoconversion can be observed. Note that the 780 nm illumination was achieved here using a two-photon laser system, but the same primed conversion event would still occur with a continuous-wave laser illumination at the same wavelength.

The present embodiments show the 3D confinement of spectral shift using a spectral shift methodology. Importantly, although we exemplify the situation where two lasers are needed to achieve a primed conversion event, each of these designs can be easily modified to accommodate more than two lasers when more lasers are required to achieve the photomodulation at the focus. In the case of multiple lasers, the additional lasers required are considered to be additional "priming" or "converting" beams.

In light of the aforementioned drawback of Dendra2 and Kaede photoconversion, four systems are established that allow 3D confined photoconversion of these and other photoconvertible/photoactivatable/photoswitchable FPs. These systems are dependent of a reliable method of conversion by illuminating the FP simultaneously with two focused continuous wave lasers in a scanning confocal microscope setup. This is referred to as primed conversion.

Figure 3:
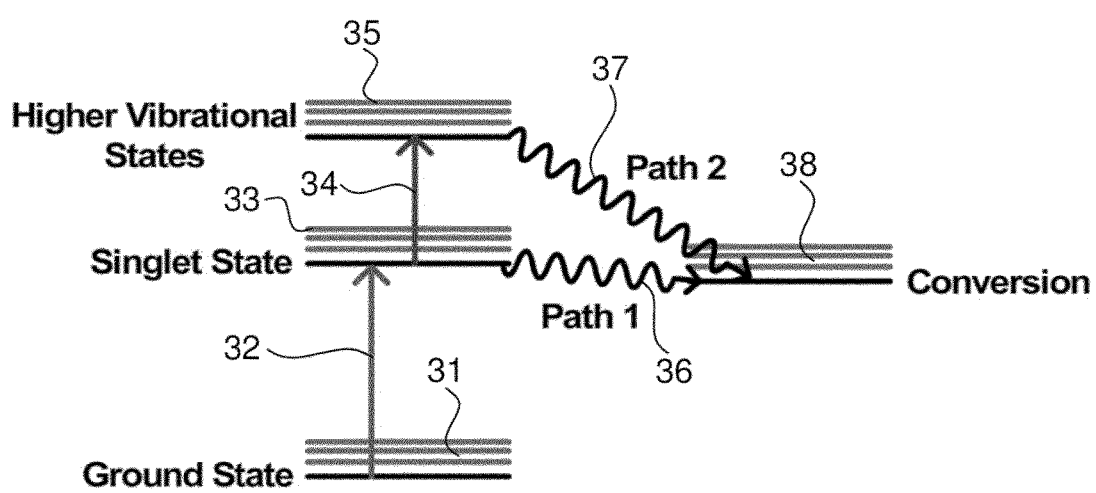
FIG. 3 shows an a general energy level diagram, particularly a Jablonski diagram describing one particular scheme of primed conversion, particularly photomodulation.

FIG. 3 shows an energy level diagram, particularly a Jablonski diagram, describing one possible description or particular scheme of a primed conversion event. The priming beam 32 brings the fluorophore from a low energy level 31, particularly the ground state to a set of higher energy levels 33, or priming energy levels, particularly the first singlet excited state or an reaction intermediate. The converting beam 34 brings the fluorophore from this initial priming/primed energy level 33, particularly the first singlet excited state, to an even higher set of energy levels 35, particularly a higher excited state or the conversion level. Bond cleavage and thus photoconversion can be accessed by traversing the landscape from either the first set of priming energy levels, particularly the first singlet excited state (reference numeral 36 as path 1) or the higher energy levels, particularly the conversion energy level (reference numeral 37 as path 2). However, path 2 traverses a more favorable part of the landscape than Path 1, allowing more efficient photoconversion towards the photoconverted, relaxed or photomodulated state 38.

It is determined here that photoconversion can be achieved for both proteins reliably at wavelengths further away from the UV spectrum (i.e. without using a 405 nm laser line) using primed conversion. One particular scheme of primed conversion can be summarized in the following manner:

(1) use a single photon, particularly within the linear absorption spectrum of the FP, to excite a fluorescent molecule (e.g., an FP) or another probe as defined before by causing an electron transition up to a set of energy levels 33, particularly the first singlet excited state, or the primed energy level—the molecule is referred to (the excited protein) as being "primed" at this point, and the laser that provides this photon will be referred to as the "priming beam."

(2) Then, before the excited molecule/protein (or probe), particularly the excited electron, relaxes back to a lower energy state, particularly the ground state 31 (which takes about a few nanoseconds in the case of the first singlet state, for example), it is further excited to a higher set of energy levels 35, particularly converted energy level, with a photon of a different wavelength than the priming beam. It is referred to the laser that provides the second photon as the "converting beam", i.e. the converting laser light beam.

(3) The energy landscape can then be traversed efficiently to the photomodulated state 38 (where the FP is photoconverted in the case of photoconvertible proteins). This process is particularly facilitated by the doubly excited electron that can transverse the energy landscape efficiently to the photoconverted state 38 causing the FP to be photoconverted.

Note that the converting beam could operate on the excited FP or probe or molecule while it is in a variety of states (e.g., the first singlet excited state, fluorescing state or any state between), as long as it is not in the ground state. The key is that the double excitation (double excitation refers to the transitioning of the probe through the priming energy levels and particularly through the converted energy level), takes the electron of the FP to a higher excited state or converted energy level that is not accessible with either the priming or converting photon, i.e. the priming and converting beam, alone. This higher conversion energy level can be different than the state achieved by 405 nm photoconversion, but this possibility should not be ruled out. If this higher excited state particularly is accessible with the 405 nm laser, photons of 405 nm can induce efficient conversion alone. Seen in this light, we see that the photon energy of either the priming or converting beams would necessarily be lower than that of the 405 nm UV laser, thus phototoxic effects will be much reduced in live specimens with primed conversion, making this process a beneficial method of photoconversion on its own even without worrying about 3D confinement.

In the scheme described above, though pulsed or modulated lasers could provide better efficiency, continuous wave lasers work well, since all excitation steps may involve linear absorption such as the possible energy landscape traversal outlined in FIG. 3.

The scheme above can be generalized to include the cases where either or both of the priming (1) and converting (2) processes would involve multiple, rather than just one, photons. In this case, it might be necessary to employ the appropriate pulsed lasers to achieve efficient excitation probability. Pulse shaping as explained in B. Xu, J. M. Gunn, J. M. Dela Cruz, V. V. Lozovoy, M. Dantus, JOSA B 23, 750 (2006) will be considered as a possible means to make the spectral shift process more efficient.

In order to take advantage of primed conversion, two lasers must be focused at the sample simultaneously. Although primed conversion requires (at least) two, particularly energetically distinct photons to function properly, this is not a coherent two-photon process, since the photons do not need to strike the fluorophore simultaneously in order to make this occur as in FIG. 3. Thus, on its own, primed conversion is not necessarily confined in 3D. However, since two lasers are required simultaneously, clever geometries can be designed to achieve reliable confined conversion in 3D. In this specification, four basic designs for efficient 3D confined primed conversion are presented as embodiments.

Figure 4:
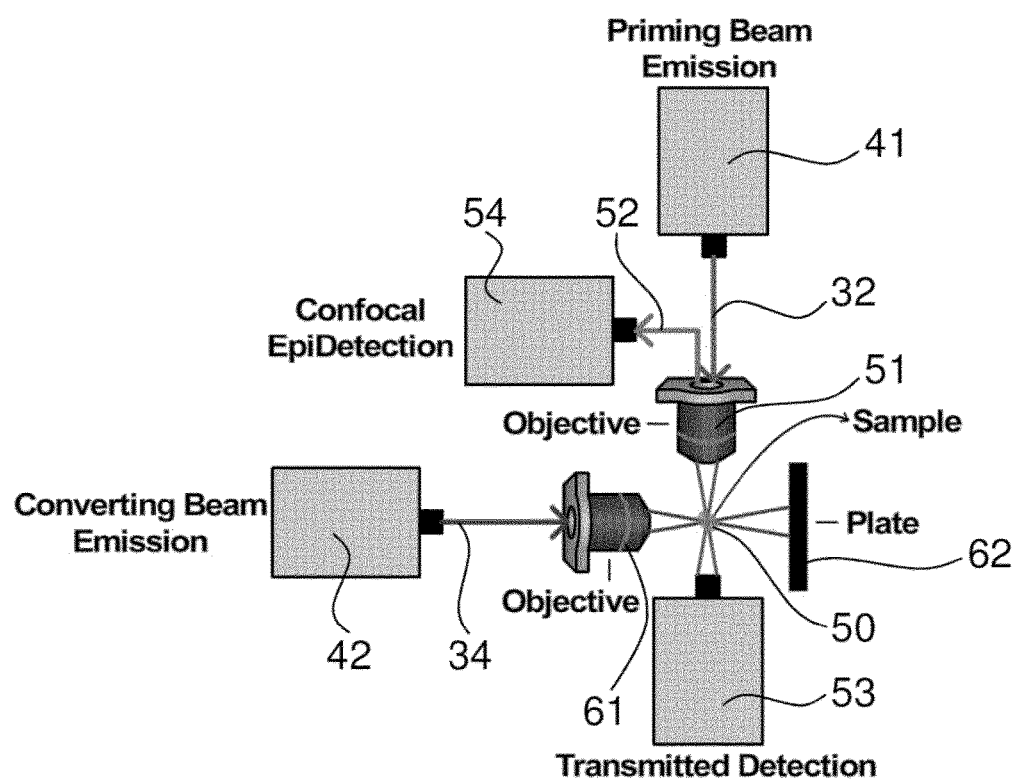
FIG. 4 shows a schematic view of a first embodiment with a crossed beam primed conversion, particularly photomodulation

FIG. 4 shows a schematic view of a first embodiment with a crossed beam primed conversion. In this design, the priming beam 32 proceeds through a standard confocal microscope setup, illuminating a sample 50 by focusing through an objective 51. The fluorescence 52 can be collected in the confocal epi-detection 54 and the beam can be refocused after the sample 50 into a transmitted detector 53 as well. The converting beam 34 is emitted into an objective 61 that is mounted at an angle (shown orthogonally in FIG. 4, but could be positioned between 0 and 180 degrees) to the first objective 51 so that the two beams 32 and 34 meet within the sample 50 at their exact foci. The converting beam 34 does not need to be detected, so it can propagate into a plate 62 after the sample 50.

In this design (FIG. 4), a confocal system is set up so that the two lasers 41 and 42 of differing wavelength can be focused simultaneously onto a specimen 50 by having the beams focus onto an individual spot in an orthogonal geometry. In this geometry, the priming beam (e.g. the beam set at 488 nm in the case of Dendra2 and Kaede) can be setup such that it is reflected in a normal confocal path to visualize the excited FPs before, during, and after conversion. This will be the standard objective 51 and 61 in the confocal microscope setup. The converting beam 34, which is placed at an angle (between 0 and 180 degrees) to the priming beam 32 and is focused on the same spot as the priming beam, can be directed immediately into a plate 62, because it will not be used to visualize the FP itself. Thus, a custom microscope setup is to be modified with a device that focuses the converting beam 34 into the same spot where the priming beam 32 will focus, without worrying about adding more detectors into the setup. A 90-degree angle between the two beams would provide the smallest overlap between the two focal regions in area 50, thus yielding the best 3D-confined primed conversion. However, angles different than 90 degree (which might be necessitated by spatial constraint issues) would also work, with the expected degradation in the 3D confinement, since the beams 32 and 34 overlap at more than just their focus spot.

Figure 5:
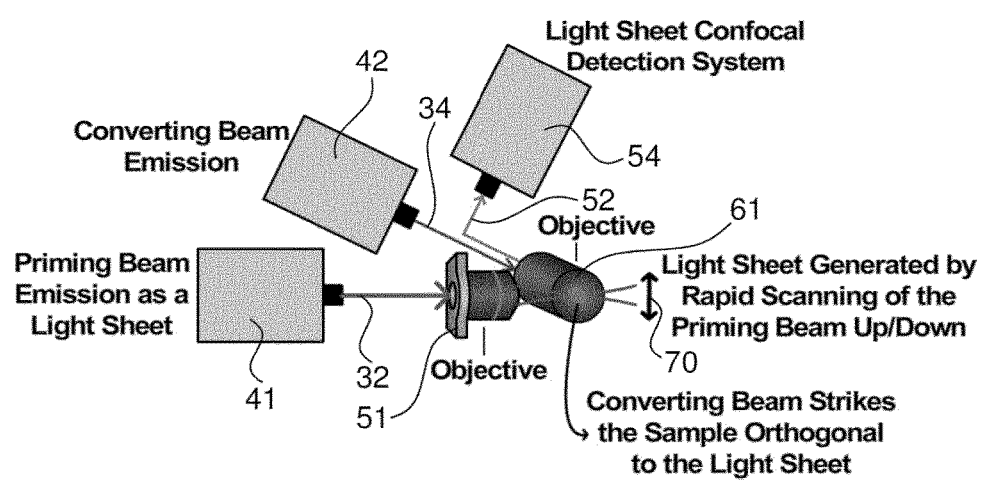
FIG. 5 shows a schematic view of a second embodiment with a SPIM primed conversion, particularly photomodulation FIGS. 6A & B show a schematic view of a third embodiment with a single objective beam primed conversion and examples of conversion plates.

FIG. 5 shows a schematic view of a second embodiment with a SPIM primed conversion. In this design, a custom selective plane illumination microscopy (SPIM) setup is to be modified in a similar manner as in the design shown in FIG. 4. In an SPIM modality, the collection objective 61 is orthogonal to an objective 51 (or set of objectives) that define the light sheet 70, generated by rapid scanning of the priming beam up and down. In this design, the priming beam 32 will be the light sheet itself, and the detection objective 61 can be adapted such that detection can be briefly turned off such that the converting beam can be directed out of the objective onto a particular spot within the specimen that is illuminated continuously by the light sheet, resulting in 3D confined conversion. Thus, a custom SPIM setup needs to be modified by a device that focuses a converting beam 34 through the detection objective 61 so that the conversion occurs within a spot that is imaged by the light sheet. Alternatively, a second objective immediately across from the detection objective can be mounted similarly as described in design of FIG. 4 such that the converting beam 34 can be focused into an area illuminated by the light sheet for confined 3D conversion again. This design has the advantage of imaging speed after conversion: immediately following conversion, fast image acquisition inherent to the SPIM design will allow measurement of converted FP dynamics/diffusion with unparalleled time resolution. Additionally, multiple converted spots spaced far apart can be imaged simultaneously in a wide field-of-view, making this an attractive option for tracking converted cells/subcellular compartments in vivo.

Figure 6:
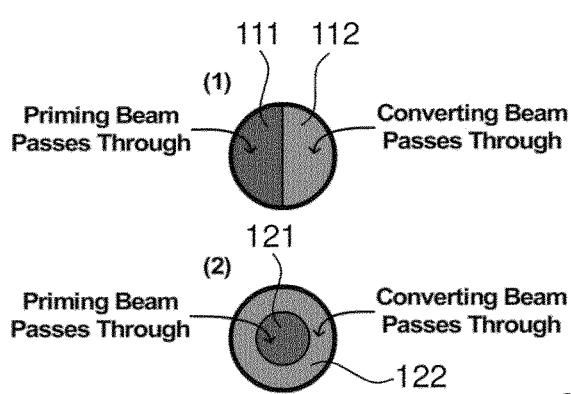
Figure 6:
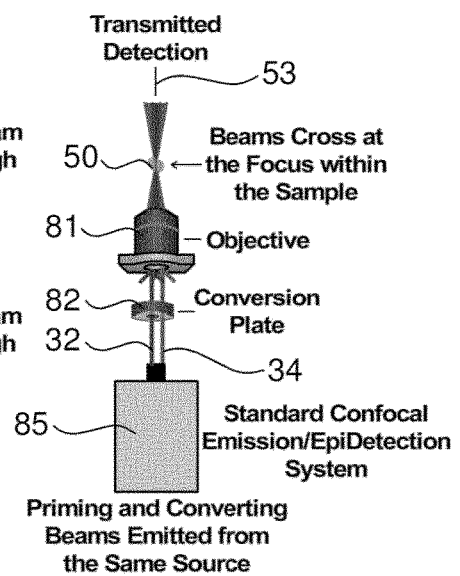

FIG. 6 shows a schematic view of a third embodiment with a single objective beam primed conversion in two parts: FIG. 6A and FIG. 6B. This design relates to a single objective crossed beam primed conversion. In this design according to FIG. 6B, a piece 82 can be mounted behind an objective 81 (e.g. in place of a DIC prism) such that the priming and converting beams 32 and 34 can be sent through the same objective 81 into the sample 50. The piece, which is a conversion plate, is provided in two exemplary embodiments shown in FIG. 6A.

In a side-by-side configuration—a first band pass filter 111 that only allows the priming beam 32 through to be focused within the objective will be on one side, while a second band pass filter 112 that only allows the converting beam 34 to be focused within the objective 81 will be on the other side.

In a concentric configuration—a first band pass filter 121 that only allows the priming beam 32 through to be focused within the objective 81 will make up the inner circle of the piece, while a second band pass filter 122 that only allows the converting beam 34 to be focused within the objective 81 will be a donut shape surrounding the inner circular piece.

The second part of the device will consist of the piece including the converting beam 34 and any focusing/aligning equipment necessary to guide the beam into the scan head so that it can image simultaneously with the priming beam 32. This geometry allows the priming and converting beams to only cross exactly at the focus, which means that the photoconversion will only occur at the focus (instead of within the entire volume of the sample that is imaged with the lasers included in the transmittal part of system 85), ensuring 3D confinement of conversion. This methodology is an attractive option for any microscope setup, since the device is a simple addition of components—namely the converting beam, equipment to align and focus said beam, and the conversion plate. This setup can easily sync with standard commercial software.

Small filters, particularly mirrors (conversion plates) can be fabricated to split two incoming beams of light. The light from the two beams 32 and 34 will converge only at the focus, allowing 3D confinement. These mirrors can be placed directly behind the objective 81, where the light is collimated. (1) The first design consists of two separated halves: one half allows the priming beam through but not the converting beam, while the other half allows the converting beam through but not the priming beam. (2) The second design consists of an outer "donut" surrounding an inner circle. The inner circle allows the priming beam through but not the converting beam, and the outer donut allows the converting beam through but not the priming beam.

Two lasers can be turned on simultaneously in a confocal/2-photon microscope setup. The beams are collimated before the objective 81 and are sent through either of the two pieces shown in FIG. 6A. The two beams then remain separated until converging at the focus within the sample. Fluorescence can be detected in the standard epi-direction at a transmittal detector 53 or within an epi detection system 85.

Figure 7:
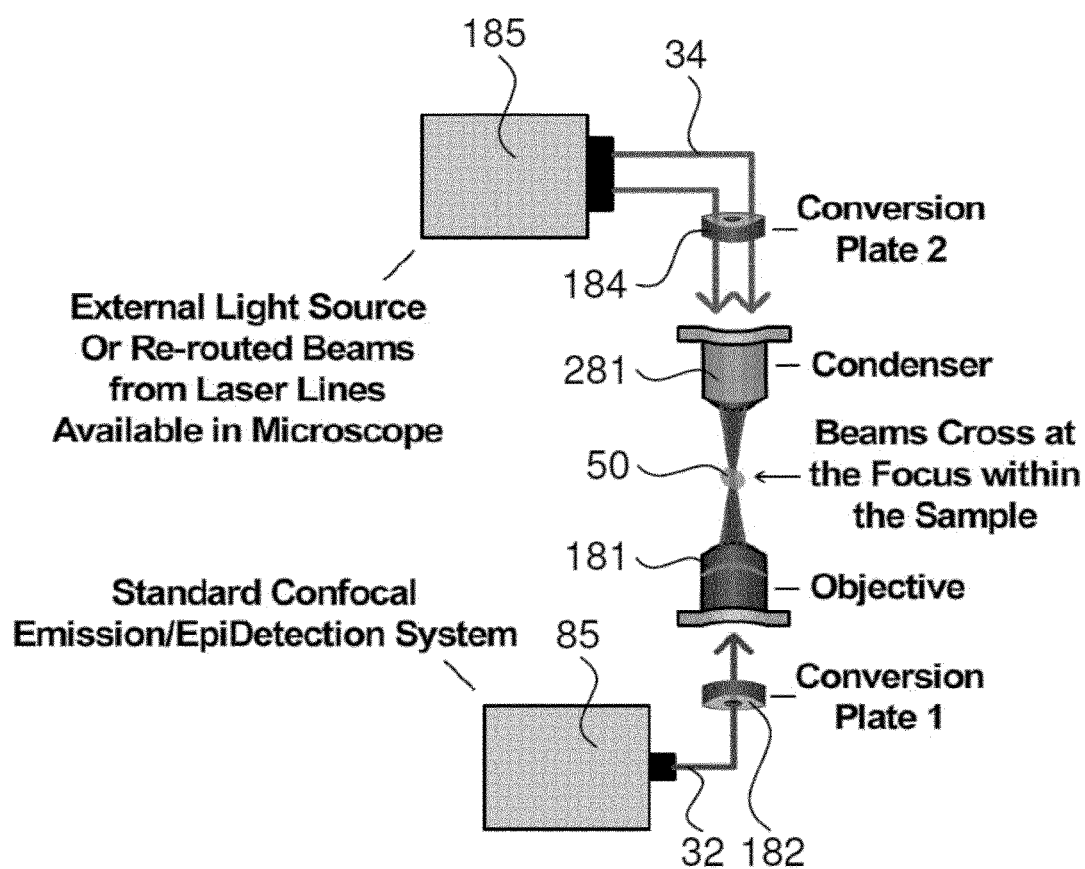
FIG. 7 shows a schematic view of a fourth embodiment with an opposing laser path primed conversion, FIGS. 8A & B show a schematic view of a fifth embodiment with a single objective beam primed conversion and examples of conversion plates.

FIG. 7 shows a schematic view of a fourth embodiment with an opposing laser path primed conversion. This design is similar to design of FIG. 6, in that the two priming 32 and converting 34 beams are collinear, and 3D confinement is achieved by ensuring that they overlap only at the common focus spot at the sample. But in this design, the two priming 32 and converting 34 beams come from opposite sides of the sample 50, one via the normal objective 181 and one from the condenser 281. Ultimately, both are focused to a common focus spot at the desired location in the sample 50.

The following points are important practical points of the design: The beam 32 coming through the objective 181 could be any of the laser lines available in the microscope. The beam 34 coming through the condenser 281 could be from an external light source 185 with appropriate turning optics mounted above the condenser 281, or could be achieved as a result of appropriate routing of one of the laser lines available in the microscope.

Either beam 32 or 34 (i.e. the one coming from the objective 181 or the one coming from the condenser 281) could be used as the either the priming 32 or the converting 34 beam, and this will be determined flexibly by practical considerations (e.g. what laser lines are available, space constraints, etc.).

Since the two beams 32 and 34 are separated before hitting the sample, there is considerable flexibility in optical design to ensure that they overlap only at the common focus point at the sample 50, therefore enabling 3D-confined primed photoconversion.

In one implementation, the top beam 32 could be masked to have only the left half of a standard circular profile, while the bottom beam 34 could be masked to have only the right half of the circular profile. This again then would ensure 3D-confined primed conversion.

In another implementation, the beam above could be masked, for example by the plate 184, to have an annular spatial profile that covers a larger numerical aperture (NA) than the bottom beam. Thus the top beam would form the focus spot with rays that come in at angles all larger than rays from the bottom beam, particularly passing through the plate 182, ensuring that they overlap only at the focus spot/focal volume, which then enables 3D-confined primed conversion. Conversely, the bottom beam could be masked to have an annular spatial profile with a larger NA than the top beam to allow 3D-confined primed conversion.

It is noted that the masks described above are similar (conceptually) when considering the conversion plates described in the design according to FIG. 6A. In the present design, one can utilize the various spatial masks that are often available in the optical path of the condenser to shape either of the two priming or converting beams. Additionally, routing the additional beam through the condenser 281 with the use of optical fibers could help facilitate the light delivery in a convenient and eye-safe manner.

Two lasers can be turned on simultaneously in a confocal/2-photon microscope setup. The beams 32 and 34 are oriented opposite one another. In this example, the beam 32 focused through the objective 181 is sent through a first conversion plate 182 similar to the "donut-beam" design described in FIG. 6A or is sent through a low NA objective. The beam 34 focused through the condenser 281 is sent through a second conversion plate 184 similar to the "donut-beam" design described in FIG. 6A. The conversion plates 182 and 184 are designed such that the two beams will only overlap at the exact focus spot within the sample. Fluorescence can be detected in the standard epi-direction in system 85.

As devices, the embodiments according to FIGS. 4 and 5 are preferred for laboratories with custom built microscope rigs, while the design according to FIGS. 6 and 7 should be versatile enough so that they can be implemented in any lab that has a standard commercial confocal microscope (e.g. Zeiss, Leica, Olympus, Nikon). Applications for utilizing these devices for 3D confined conversion include—but are not limited to—in vivo cell tracking in various model organisms for tissue development/regeneration/cancer metastasis studies, FP-protein of interest fusion trafficking and kinetics studies, and neuronal tract tracing in vivo to elucidate connections within the brain of an intact organism. Spectral shift varieties of proteins allow subpopulation tracking, which simplifies the task and greatly reduces computing power necessary for segmentation and feature extraction of dynamic biological processes (e.g. embryo development, cell movement, subcellular dynamics, etc.). These devices are useful and are—in many ways—necessary (e.g. for the proteins that cannot be converted with 2-photon lasers alone) to achieve the precise 3D targeting of subpopulations of cells labeled with spectral shift proteins as well as subpopulations of spectral-shift protein-tagged proteins of interest (e.g. spectral shift proteins tagged to transcription factors, membrane-associated proteins, extracellular component proteins, etc.) needed for subpopulation tracking.

In addition, the devices and imaging geometries described in this specification may be applied for an additional purpose—any optical reporters requiring a "priming-like" and "converting-like" dual light source modality to achieve significant fluorescence emission could be imaged (i.e., the resulting signal from the crossing of two lasers could be recorded in space and time using a detector in the microscope system) with the same principle as primed conversion. For example, if two light sources (e.g., lasers) instead of one are required to generate a signal (e.g., fluorescence), 3D confined imaging comparable to two-photon imaging can be achieved using the same devices envisioned for a primed conversion modality. In the case of fluorescence from two combined near infrared continuous wave lasers, the designs outlined in this provisional document enable 3D confined imaging in deep tissue applications—since the optimal "tissue transparency window" is in the near infrared regime (~600 nm to ~1300 nm)—significantly reducing the need for costly two-photon laser sources. Clearly, the designs can be extrapolated to an even greater number of lasers, if necessary, with simple modifications. Thus, all four proposed designs will be useful for a wide variety of imaging challenges and will benefit the biological imaging community as a whole.

Importantly, the alignment of the illuminating light such that the foci of the converting and priming beam are completely overlapping is of great importance for efficient primed conversion to occur. As a result, a controller or software module is to be implemented as known by persons skilled in the art to ensure that the lasers—2 or more, depending on the number of photons needed for the primed conversion or spatially confined excitation event to occur—are perfectly aligned at the focus, especially in custom microscope systems and in commercial systems where lasers must be directed into the microscope in multiple locations.

Thus, all four embodiments will be useful for a wide variety of imaging challenges and will benefit the biological imaging community as a whole.

Figure 8:
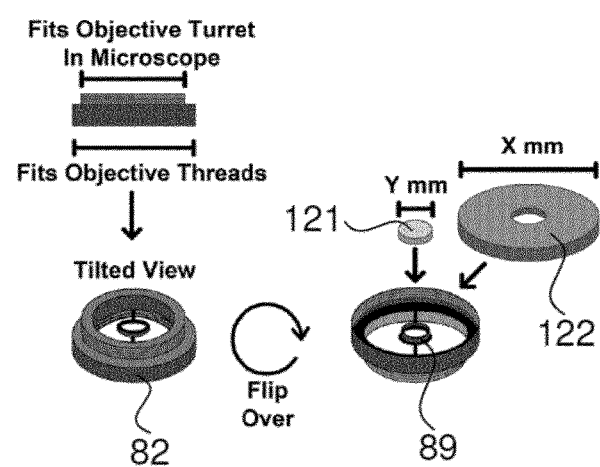
Figure 8:
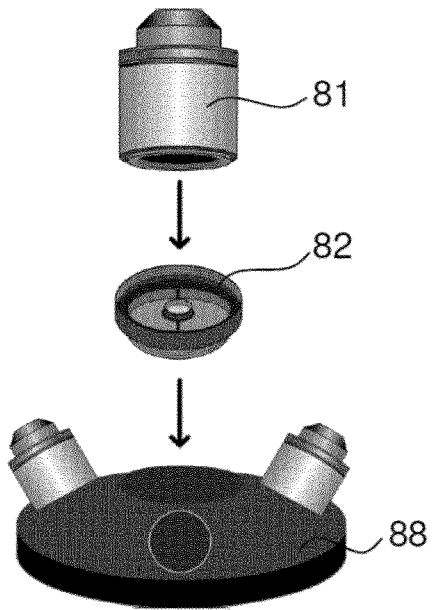

FIGS. 8A and 8B show a schematic view of a fifth embodiment with a single objective beam primed conversion and examples of conversion plates. The embodiment comprises a small metal or plastic piece 82 that fits into the objective turret of a wide-field, confocal or two-photon laser scanning microscope—for example, with standard M27 (27 mm) objective port threads. By flipping the device over, it can be appreciated that there are two sets of threads, and a frame section 89 where two glass dichroic mirrors will fit into place. The larger glass donut-shaped dichroic (with max diameter, X) 122 passes the priming beam 32, while the smaller glass disk dichroic (with diameter, Y) 121 passes the converting beam 34. Alternatively, the larger donut-shaped dichroic 122 may pass the converting beam 34, while the smaller glass disk 121 passes the priming beam 32. Once the glass dichroics are in place, an objective lens can be threaded onto the device on the larger side. The entire objective and device together can then be threaded onto an objective port of a wide-field, confocal or two-photon laser scanning microscope. When the priming and converting beam illuminate the sample through the invention, a confined photomodulation (e.g., photoconversion) or excitation event can occur at the focus. It is noted that a device allowing the passage of more than two lasers can also be envisioned by adding concentric donut shaped dichroics or by partitioning the whole area in a different way. Additionally, the photoexcitation/photomodulation device can be modified such that it fits anywhere within the light path of the microscope, for example within the filter cube area that sits within the collimated region of the laser, before the objective.

Figure 9:
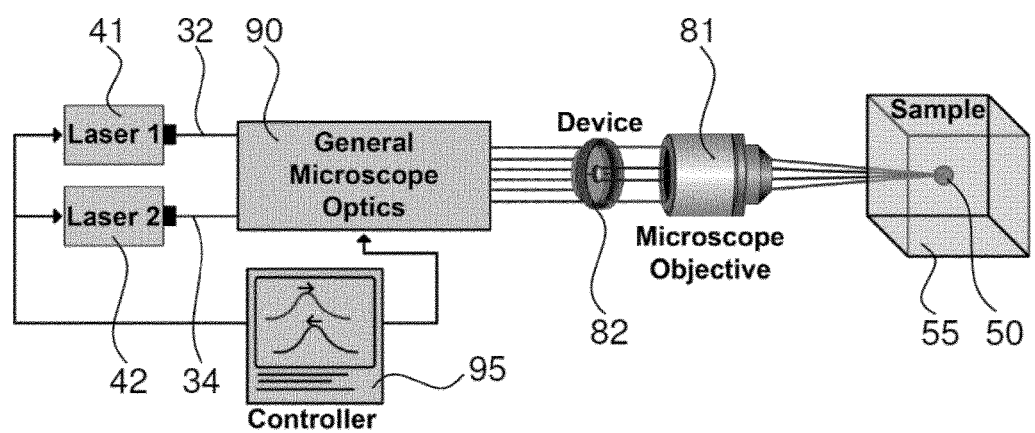
FIG. 9 shows a general representation of a system according to an embodiment of the invention.

FIG. 9 shows a general representation of a system according to an embodiment of the invention. As the device is intended for use in any microscope system (i.e., custom home-built or commercial), the implementation/methodology for the use of the device is also explained here. First, the system must be equipped with the proper laser combination 41, 42 to enable a primed conversion or localized excitation event. If the system requires the addition of another laser (ideally an inexpensive continuous-wave laser source), this laser must be coupled into the device with the following consideration in mind: the priming 32 and converting 34 beam must meet at the focus 50, or else the event will not occur. Thus, a specific predetermined software or controller element 95 is provided for the device to control the optics 90 within the microscopy system so that the lasers 41, 42 are aligned to meet at the focus 50. For example, the control software 95 should manipulate moving optical components (e.g., mirrors, periscopes, prisms, etc.) within the microscope system 90 that could affect the positioning of the priming 32 and/or converting 34 beams to allow maximum overlap only at the focus 50 in the sample area 55.

For applications with primed conversion, one can envision the following possibilities for the device: (1) if subsequent imaging requires a different light that is not passed by either dichroic, the device will be removed before imaging, or (2) if subsequent imaging can proceed with a light source that passes through either dichroic, the device may stay in place. Importantly, applications involving 3D confined optical excitation will require the device to remain in place throughout the imaging time, and outcoming signal from the sample (e.g., fluorescence) will be detected at a detector after the sample is illuminated by the crossed beams—for example in the epi- or trans-directions as well as in any isotropic direction surrounding the focal plane.

As before, modifications in the device according to FIG. 9 that would allow more lasers to achieve the primed conversion or confined excitation event can be easily extrapolated from this control flow design by the introduction of more lasers into the setup (directed into the general microscope optics 90). In this case, the control software 95 would have to ensure that all of the lasers 41, 42 etc. meet at the focus 50 together.

The devices and imaging geometries described in this specification may be applied for an additional purpose—any optical reporters requiring a "priming-like" and "converting-like" dual light source modality to achieve significant fluorescence emission could be imaged (i.e., the resulting signal from the crossing of two lasers could be recorded in space and time using a detector in the microscope system) with the same principle as primed conversion. For example, if two lasers 41, 42 instead of one are required to generate a signal (e.g., fluorescence), 3D confined imaging comparable to two-photon imaging can be achieved using the same device envisioned for a primed conversion modality described above. In the case of fluorescence from two combined near infrared continuous wave lasers, the designs outlined in this document enable 3D confined imaging in deep tissue applications. As mentioned above, the design of the device and the components (e.g., number of lasers, complexity of the controller, etc.) can be extrapolated to an even greater number of lasers, if necessary, with simple modifications.

Within the following paragraph an explanation of the control flow of the device as an exemplary embodiment of the methodology for the patent, including the following steps:
(i) Connect the required number (2 or more) of light sources 41, 42 (e.g., laser sources) to the microscope system 90.
(ii) Install the conversion device 82 into the system—for example by threading one side into an objective port and the other into a microscope objective 81.

(iii) Connect and apply the controller software or hardware 95 to the microscope system 90 and use e.g., a test sample of nano- or micron-sized beads to allow the software to control the hardware such that the lasers 41, 42 are all aligned at the same focal volume 50 reliably.

(iv) Place the sample on the microscope stage and focus the objective 81 into a region of interest.

(v) Illuminate the sample 50, 55 simultaneously with both lasers 41, 42 to achieve a primed conversion event or to achieve confined excitation within the sample.

a. In the case of primed conversion continue with imaging either by removing the device and illuminating the sample with a different light source or use a subset of the total number of lasers to illuminate the sample and collect the subsequent signal using an imaging detector (e.g., photo-multiplier tube, avalanche photodiode, etc.).

b. In the case of confined excitation, collect the signal emanating from the sample being illuminated by any number of lasers 41, 42 (greater than two, to generate the confined excitation event) using an imaging detector 85 (e.g., photomultiplier tube, avalanche photodiode, etc.).

Figure 10:
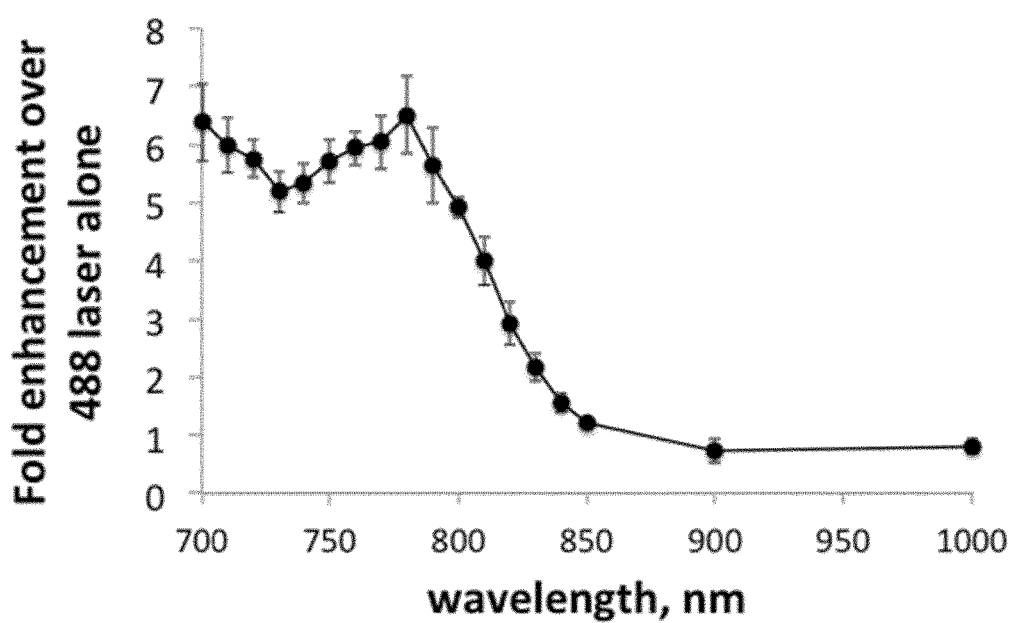
FIG. 10 shows that the converting beam, can have a range of acceptable wavelength values to achieve the primed conversion/photomodulation effect.

FIG. 10 shows that primed conversion can be achieved with a range of wavelengths, in this example with the protein Dendra2. For a given priming beam 32 wavelength of 488 nm (in this case), the converting beam 34 wavelength necessary to achieve an efficient primed conversion event can be as high as 850 nm, and the range extends down into the visible spectrum below 700 nm. Note that the trend continues into the visible spectrum (i.e., below 700 nm), but the characterization was only performed for wavelengths between 700 nm and 1000 nm in this example. It is worth noting that the priming beam 32 can also be a range of wavelengths around the peak absorption of 488 nm in the case of Dendra2 (e.g., 458 nm from the same laser source).

Figure 11:
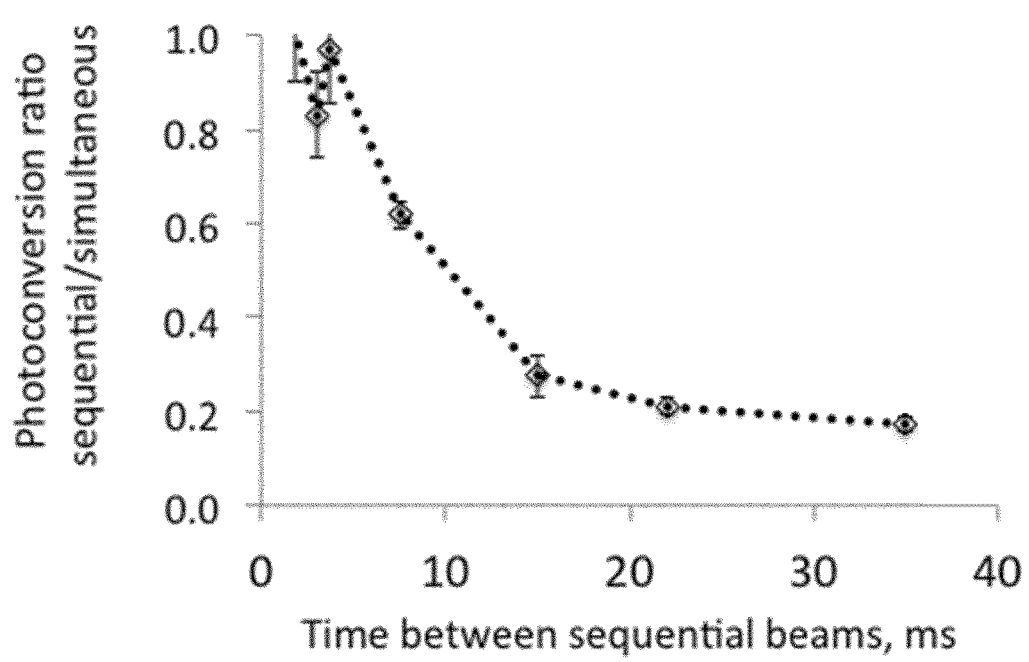
FIG. 11 shows that the converting beam can illuminate the sample after the initial priming beam illumination and still achieve the primed conversion/photomodulation event

FIG. 11 illustrates that the primed state 33 can have a lifetime that is longer than the fluorescent state of the fluorescent protein itself. The fluorescent state lifetime is normally on the order of nanoseconds. Interestingly, the protein Dendra2 was illuminated with the priming beam 32 (in this case at 488 nm). Then, a time delay was imposed before illuminating the sample with the converting beam 34. For the protein Dendra2, efficient primed conversion can be achieved even ~5 milliseconds after illuminating with the priming beam 32. In the case of Dendra2, the primed conversion efficiency decreases with time delays longer than a few milliseconds. Thus, it can be envisioned that there exist other proteins besides Dendra2 where the primed conversion process can be achieved after a significant time delay. This property could be useful for applications in spectroscopy as well as for implementations of FIGS. 5-7 that require that the two lasers not be on simultaneously for fear of bleaching other non-photomodulatable fluorescent proteins in the tissue.

Figure 12:
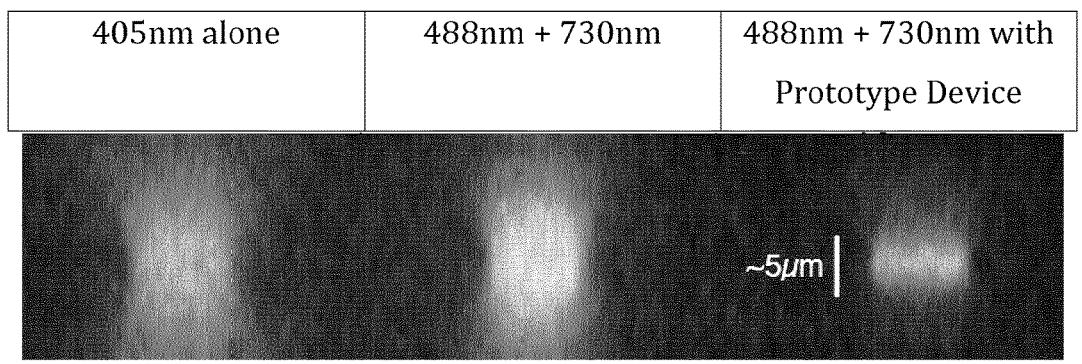
FIG. 12 shows spatial confinement of the primed conversion of the protein Dendra2 using a prototype device as described in FIG. 6

FIG. 12 shows the results of primed conversion resulting from an implementation of the phenomenon using a prototype device outlined in FIG. 6B. In all three panels, the protein Dendra2 was embedded in polyacrylamide so that diffusion of the fluorescent protein would be limited during the photoconversion trials. Each image is a stack of individual optical sections in a single axial plane, imaged parallel to the illumination direction. The axial plane refers to the X-Z plane, where the X direction corresponds to an axis perpendicular to the illumination at the sample 50 while the Z direction corresponds to an axis parallel to the illumination at the sample 50. The sample was illuminated from below and brought to a focus at the center of the image. Only the channel showing the photoconverted (red) state of the fluorescent protein Dendra2 is depicted. When the protein Dendra2 is illuminated with a continuous wave 405 nm laser alone, the photoconversion is not confined (>10 µm) in the axial "Z" direction, as the signal can be seen above and below the center focal region. When a 488 nm and 730 nm laser illuminate the sample simultaneously, a similar photoconversion event can be seen, but the photoconversion is still not confined (>10 µm). When the conversion plate 82 is in place on the device depicted in FIG. 6B while the 488 nm and 730 nm lasers illuminate the sample, the photoconversion is confined (<10 µm).

Figure 13:
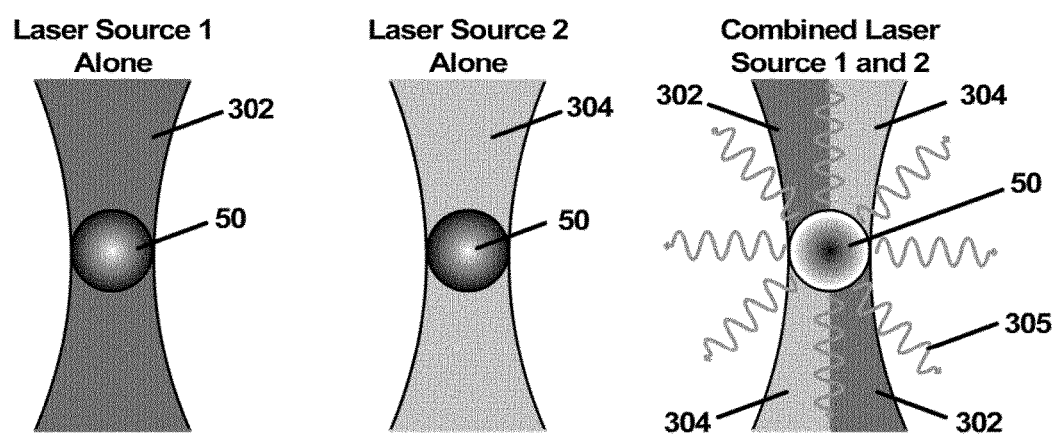
FIG. 13 shows a schematic view of confined excitation as an extension of primed conversion

Importantly, each of the designs outlined in this section can be easily extrapolated for the case of confined photoexcitation. We exemplify this concept by considering the device designs outlined in FIG. 6 and FIG. 8. However, it is important to mention that confined photoexcitation can also be achieved with the other designs as in FIG. 4, FIG. 5, and FIG. 7, as well as any modifications to these designs required to enable more than two lasers to meet at the focus. In FIG. 13, we illustrate the primed excitation event for the simplified case of two-beam illumination in a focused microscopy setup. In this embodiment, laser 302 is set at one wavelength while laser 304 is set at a second differing wavelength. When either laser 302 or 304 is focused onto the sample 50 alone (see left panel and center panel), the fluorescent protein or probe does not emit any photons within the wavelength band that you are detecting. However, when the sample 50 is illuminated with both lasers 302 and 304, the sample 50 emits photons 305 within the detected wavelength band. Note that this confined photoexcitation embodiment may be easily extrapolated to a situation where more than two illuminating light sources are needed to simultaneously illuminate the sample 50 to cause the photon emission 305 event.

Figure 14:
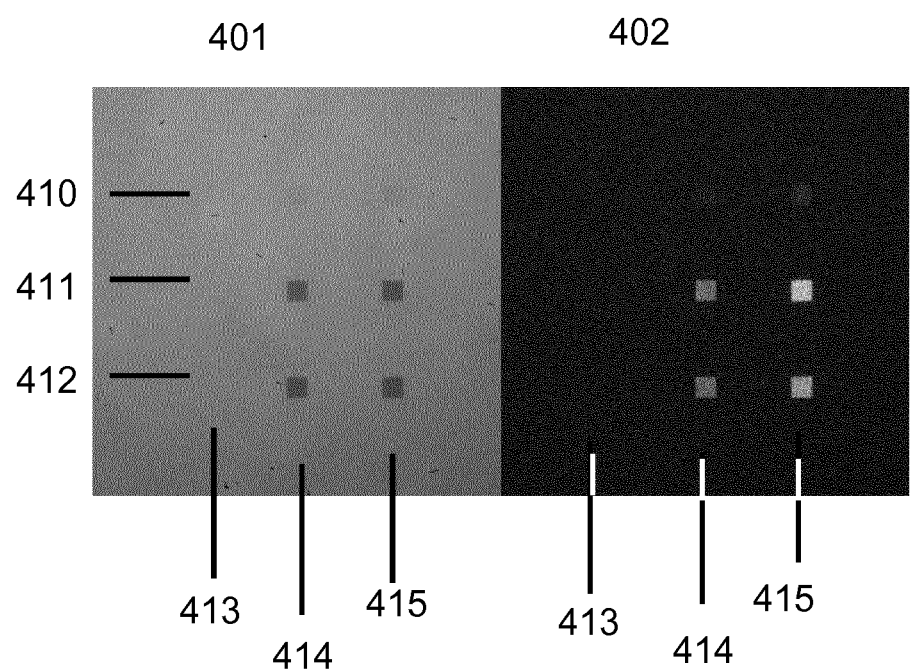
FIG. 14 shows primed conversion/photomodulation of mEOS2, monomeric EOS2

FIG. 14 shows an example where photomodulation has been achieved using the photoconvertible protein mEos2 (as described in McKinney et al., Nature Methods, February; (6):131-133, (2009)). mEos2 emits fluorescence in a green fluorescence channel 401 and can be converted to a different state, where it emits in a red spectrum. The left panel shows data from the green channel 401, while the right panel 402 shows data from the red spectral channel. The right panel 402 therefore shows the amount of photoconverted protein after illumination. Each row 410, 411, 412 corresponds to a different priming wavelength (top: 458 nm 410, middle: 488 nm 411, bottom: 514 nm 412), while each column represents a different combination of lasers (left column: converting beam alone, 413, middle column: priming beam (730 nm CW) alone 414, right column: priming beam with converting beam together 415). The rightmost columns are the brightest, especially when 488 nm is used as the priming beam in conjunction with the 730 nm converting beam. This figure shows another example of how primed conversion can be seen as a general phenomenon.

An alternative set of claims that is comprised in the content of this application as well could be formulated as follows:

In a first independent claim of said alternative claims set, one could claim:

A method to achieve spatially confined photomodulation at the focal volume 50, 55 of a microscope, comprising two or more laser light sources 41, 42 emitting light 32, 34 of different wavelengths adapted to excite a material in an identical number of independent excitation steps to a higher vibrational state from which the material relaxes emitting a conversion light 37 to be detected.

A second claim of the alternative claim set could refer to the first independent claim of the alternative claim set, disclosing the method, wherein a control unit 95 is provided to control the emission of the laser light sources 41, 42 and the method comprises the step of controlling the microscope optics 90 to focus the beams from the laser light sources 32, 34 onto the focal volume 50, 55.

A third claim of the alternative claim set could refer to the second claim of the alternative claim set, disclosing the method, wherein the beams from the laser light sources 32, 34 are only intersecting one another within the focal volume 50, 55.

A fourth claim of the alternative claim set could refer to the first independent claim of the alternative claim set, disclosing the method, comprising the steps of:
- connecting the predetermined number of two or more laser light sources 41, 42 to the microscope system 90,
- installing a conversion device 82 into the system 90, preferably by threading one side into an objective port and the other into a microscope objective 81,
- connecting and applying a controller software or hardware 95 to the microscope system 90 and adjusting the lasers light sources 41, 42 to align all at the same focal volume 50,
- placing the sample on the microscope stage and focus the objective 81 into a region of interest,
- illuminating the sample 50, 55 simultaneously with all lasers light sources 41, 42 to achieve a primed conversion event or to achieve confined excitation within the sample.

A fifth claim of the alternative claim set could refer to the fourth claim of the alternative claim set, claiming the method wherein in the case of primed conversion, the method comprises the step of continuing with imaging either by removing the device and illuminating the sample with a different light source or use a subset of the total number of lasers to illuminate the sample and collect the subsequent signal using an imaging detector 85.

A sixth claim of the alternative claim set could refer to the fourth claim of the alternative claim set, claiming the method, wherein in the case of confined excitation, the method comprises the step of collecting the signal emanating from the sample being illuminated by any number of lasers 41, 42 using an imaging detector 85.

A seventh claim of the alternative claim set could disclose a system to achieve spatially confined photomodulation at the focal volume 50, 55 of a microscope comprising two or more laser light sources 41, 42 emitting light 32, 34 of different wavelengths adapted to excite a material in an identical number of independent excitation steps to a higher vibrational state from which the material relaxes emitting a conversion light 37 to be detected, wherein the system further comprises an optical device to be attached in the light path of said microscope comprising at least one optical imaging element for every laser light source to be collimated at the focal volume 50, 55 of the microscope.

An eighth claim of the alternative claim set could refer to the seventh claim of the alternative claim set disclosing the system, wherein the beams from the laser light sources 32, 34 are only intersecting one another within the focal volume 50, 55.

An ninth claim of the alternative claim set could refer to the seventh claim of the alternative claim set disclosing the system, wherein the system comprises two laser light sources 41, 42 and the optical imaging element comprises a optical disc comprising a first portion adapted to transmit and collimate one of the laser light beams 32 or 34 and a complementary second portion adapted to transmit and collimate the other of the laser light beams 34 or 32.

A tenth claim of the alternative claim set could refer to the seventh claim of the alternative claim set disclosing the system, wherein the two portions comprise halves 111, 112 of a transmitting collimating lens.

An eleventh claim of the alternative claim set could refer to the seventh claim of the alternative claim set disclosing the system, wherein the two portions comprise two concentric portions 121, 122 of a transmitting collimating lens.

A twelfth claim of the alternative claim set could refer to the seventh claim of the alternative claim set disclosing the system, wherein system comprises a scanner moving the beam of one of the laser light sources 41 to generate a light sheet.

LIST OF REFERENCE SIGNS

| | |
|---|---|
| 11 | cytoplasmic unconverted Kaede filling |
| 12 | intended conversion area |
| 13 | arrow indicating conversion attempt region |
| 21 | cytoplasmic unconverted Dendra2 filling |
| 22 | intended conversion area |
| 23 | arrow indicating conversion attempt region |
| 24 | visible light area |
| 31 | low energy level |
| 32 | priming beam |
| 33 | intermediate, priming or primed energy level |
| 34 | converting beam |
| 35 | higher or conversionenergy level |
| 36 | path 1 |
| 37 | path 2 |
| 38 | conversion state |
| 41 | priming beam laser |
| 42 | conversion beam laser |
| 50 | focus area/sample area |
| 51 | objective |
| 52 | fluorescence |
| 53 | transmission detector |
| 54 | confocal epi detector |
| 55 | sample area |
| 61 | objective |
| 62 | plate |
| 70 | scanning fort he light sheet |
| 81 | single objective |
| 82 | conversion piece |
| 85 | emission and detection system |
| 88 | microscope turret |
| 89 | optical frame |
| 90 | microscope optics |
| 95 | control unit |
| 111 | first beam filter |
| 112 | second beam filter |
| 121 | first beam filter |
| 122 | second beam filter |
| 181 | objective |
| 182 | first conversion plate |
| 184 | second conversion plate |
| 185 | external light source |
| 281 | condenser |
| 302 | excitation beam 1 |
| 304 | excitation beam 2 |
| 305 | emitted photon |
| 401 | green channel |
| 402 | red channel |
| 410 | priming beam of 458 nm |
| 411 | priming beam of 488 nm |

-continued

| LIST OF REFERENCE SIGNS | |
|---|---|
| 412 | priming beam of 514 nm |
| 413 | converting beam alone |
| 414 | priming beam alone |
| 415 | priming and converting beam |

The invention claimed is:

1. A method for spatially confined photomodulation or photoexcitation at a focal volume (50) of a microscope system (90), comprising the steps:
providing means (41, 42, 85, 185) to generate a priming laser light beam (32, 302) comprising a priming wavelength band (32, 302) and a converting laser light beam (34, 304) comprising a conversion wavelength band (34, 304) different to the priming wavelength band (32, 302),
providing a sample, comprising a photoexcitable probe, wherein said probe comprises a low energy level (31) and a primed energy level (33) having a greater energy than the low energy level (31)
illuminating the probe with the priming laser light beam, such that the probe is transitioned by photointeraetion with the priming laser light beam from the low energy level (31) to the primed energy level (33) in an excitation step,
illuminating the probe with the converting laser light beam (34, 304)
such that the probe transitions (37) to a photomodulate state (38) altering the spectral properties of the probe, or
such that said probe transitions (305) under the emission of a photon to the low energy level (31).

2. Method according to claim 1, wherein the probe further comprises a conversion energy level (35) having a higher energy than the low energy level (31) and the primed energy level (33), and wherein under illumination of the probe with the converting laser light beam (34, 304), said probe transitions from the primed energy level (32, 302) to the conversion energy level (35)
from where the probe transitions (37) to said photomodulated state (38),
or
from where said probe transitions (305) under the emission of a photon from said conversion energy level (35) to the low energy level (31).

3. Method according to claim 1, the photon emitted from the probe upon transition to the low energy level, stems from a spontaneous emission process.

4. Method according to claim 1, wherein the photomodulated state (38) is a photoconverted, photoactivated or photoswitched state of the probe.

5. Method according to claim 1, wherein the probe comprises a photoconvertible, photoswitchable or photoactivatable protein.

6. Method according to claim 1, wherein the probe is illuminated simultaneously or sequentially with the priming laser light beam (32, 302) and the converting laser light beam (34, 304).

7. Method according to claim 1, wherein the probe is illuminated with a third laser light beam comprising a third wavelength hand and wherein said third laser light beam is either a second priming laser light beam or a second convening laser light beam.

8. Method according to claim 1, wherein the priming laser light beam (32, 302) and the converting laser light beam (34, 304) are focused within the focal volume (50) of the microscope system (90).

9. Method according to claim 1, wherein the priming laser beam (32, 302) comprises a priming wavelength band that comprises at least a portion of the blue or blue/green visible spectrum, and that the converting laser light beam (34, 304) comprises a conversion wavelength hand that comprises at least a portion of the visible far red and/or near infrared spectrum.

10. Microscope system (90), comprising:
means (41, 42, 85, 185) for generating a priming laser light beam (32, 302) of a priming wavelength band and a converting laser light beam (34, 304) of a conversion wavelength band different to the priming wavelength band,
wherein the microscope system (90) comprises a photoexcitation device (51, 61, 81, 82, 181, 182, 281, 184) that is designed to superimpose the priming laser light beam (32, 302) and the convening laser light beam (34, 304) within the focal volume (50) of the microscope system (90), such that the priming, laser light beam (32, 302) the convening laser light beam (34, 304) are superimposed only within the focal volume (50),
wherein said photoexcitation device (81, 82) comprises a first objective lens (81) and a first optical element (82) arranged at the first objective lens (81), wherein said first optical element (82) comprises a first and a second portion (121, 122, 111, 112), designed to superimpose the priming and the converting laser light bean (32, 34, 302, 304), only within the focal volume (50) are passed through said first optical element (82) and the first objective lens (81), or
wherein said photoexcitation comprises a first lens (181) and a first optical element (182) threaded on the first lens (181), and a second lens (281) and a second optical element (184) threaded on the second lens (281), and wherein the first and the second optical element (182, 184) are designed such that the priming and the converting laser light beam (32, 34, 302, 304) are superimposed only within the focal volume (50).

11. Microscope system according to claim 10, wherein the first portion (111, 121) of the optical element (82) is adapted to transmit only the priming laser light beam (32, 302) and the second portion (112, 122) of the optical element (82) is adapted to transmit only the converting laser light beam (34, 304), wherein said portions (111, 112, 121, 122) comprise dichroic mirrors.

12. Microscope system according to claim 10, wherein the first and the second portion (121, 122) of the first optical element (82) are arranged concentrically (121, 122) with respect to a common center or that the first and the second portion (111, 112) of the first optical element (82) are arranged such that they each form a halve of the first optical element (82).

13. Microscope system according to claim 10, wherein said photoexcitation device (51, 61) comprises a first and a second lens (51, 61), wherein the first and the second lens (51, 61) are arranged such that the priming and the converting laser light beam (32, 34, 302, 304) are superimposed only within the focal volume (50), wherein the first and the second lens (51, 61) are arranged such that the priming and the converting laser light beam (32, 34, 302, 304) are propagated at an angle to each other.

14. Microscope system according to claim 10, characterized in that either the priming or the convening laser light beam (32, 34, 302, 304) is shaped as a light sheet after passing through the first or second lens (51, 61).

15. Microscope system according to claim 10, characterized in that the priming laser beam (32, 302) comprises a priming wavelength band that comprises at least a portion of the blue or blue/green visible spectrum, and that the convening laser light beam (34, 304) comprises a conversion wavelength band that comprises at least a portion of the visible far red and/or near infrared spectrum.

* * * * *